United States Patent [19]
Metzler

[11] Patent Number: 6,022,088
[45] Date of Patent: Feb. 8, 2000

[54] OPHTHALMIC MICROSURGICAL SYSTEM

[75] Inventor: Michael Eugene Metzler, St. Louis, Mo.

[73] Assignee: Bausch & Lomb Surgical, Inc., Claremont, Calif.

[21] Appl. No.: 08/922,114

[22] Filed: Aug. 28, 1997

Related U.S. Application Data

[60] Provisional application No. 60/025,498, Aug. 29, 1996.
[51] Int. Cl.[7] .................................................. A47B 81/00
[52] U.S. Cl. ........................................ 312/209; 312/249.8
[58] Field of Search ................................... 312/209, 223.1, 312/249.8, 250, 223.6, 223.2; 606/34

[56] References Cited

U.S. PATENT DOCUMENTS

| | | | |
|---|---|---|---|
| 4,095,859 | 6/1978 | Decker et al. | 312/209 |
| 4,572,594 | 2/1986 | Sxhwartz | 312/209 |
| 4,607,897 | 8/1986 | Schwartz | 312/209 |
| 4,933,843 | 6/1990 | Scheller et al. . | |
| 5,007,688 | 4/1991 | Bayerlein et al. | 312/209 |
| 5,112,019 | 5/1992 | Metzler et al. . | |
| 5,157,603 | 10/1992 | Scheller et al. . | |
| 5,399,007 | 3/1995 | Marconet | 312/209 |
| 5,417,246 | 5/1995 | Perkins et al. . | |
| 5,455,766 | 10/1995 | Scheller et al. . | |
| 5,518,310 | 5/1996 | Ellman et al. | 312/209 |
| 5,857,685 | 1/1999 | Phillips et al. | 312/249.8 |

*Primary Examiner*—Peter M. Cuomo
*Assistant Examiner*—Gerald A. Anderson
*Attorney, Agent, or Firm*—Grant D. Kang

[57] ABSTRACT

A cart of a system for controlling a plurality of ophthalmic microsurgical instruments is disclosed. The cart of the present invention is for supporting and transporting the operating components of the microsurgical system. The cart must allow for the various operating components to be quickly installed or for removal from the cart to properly configure the system for use in performing selected surgical procedures. The cart must provide for transporting and storage of various peripheral components.

20 Claims, 7 Drawing Sheets

Microfiche Appendix Included
(32 Microfiche, 6294 Pages)

figure 1 figure 2 figure 3 figure 4 figure 5 figure 7

OPHTHALMIC MICROSURGICAL SYSTEM

This application claims benefit of provisional application Ser. No. 60/025,498 filed Aug. 29, 1996.

MICROFICHE APPENDIX

This application includes a microfiche appendix which is a copy of the provisional application under which priority is claimed.

BACKGROUND OF THE INVENTION

This invention relates generally to microsurgical and ophthalmic systems and, particularly, to a cart for supporting and transporting components of such microsurgical systems.

Present day ophthalmic microsurgical systems provide one or more surgical instruments connected to a control console. The instruments are often electrically or pneumatically operated and the control console provides electrical or fluid pressure control signals for operating the instruments. The control console usually includes several different types of human actuable controllers for generating the control signals supplied to the surgical instruments. Often, the surgeon uses a foot pedal controller to remotely control the surgical instruments.

Microsurgical and ophthalmic systems are relatively costly and are often purchased by hospitals and clinics for sharing among many surgeons with different specialties. In eye surgery, for example, some surgeons may specialize in anterior segment procedures, while other surgeons may specialize in posterior segment procedures. In performing the various procedures, surgeons use a number of different surgical instruments, such as those previously discussed. Electronic controls for controlling the various instruments are preferably located close to the surgeon while performing the procedures for facilitating adjustment and control of the instruments.

Present microsurgical systems, such as those disclosed in U.S. Pat. Nos. 4,933,843, 5,157,603, 5,417,246 and 5,455,766, typically comprise consoles with fully integrated electronic controls which allow one or more instruments to be connected to the console for performing particular procedures. The electronic controls are programmable so that various instruments may be connected to the console. To transport the system, it has generally been known to place the console on a movable cart, such as that disclosed in U.S. Pat. No. 5,112,019.

These prior art systems can be inconvenient and inefficient for performing multiple ophthalmic microsurgical procedures. Because the electronic controls are fully integrated into the console, the prior art microsurgical systems cannot be expanded to incorporate additional instruments beyond those accommodated by the console. To do so would require purchasing an additional console, which is quite costly. Additionally, the foot pedal control, disposable packs and other items used during the procedures are stored and carried separately from the prior art system and may become lost or separated from the system during transport. Locating and storing these items remote from the system imparts the inconvenience of having to search for and assemble the items before (or during) surgery.

Furthermore, in conventional systems, the cables which interconnect the console and peripherals such as the foot pedal control assembly and IV pole assembly hang loosely in the open. Additionally, peripherals such as the IV pole assembly are commonly mounted on the exterior of a cart as shown in U.S. Pat. No. 5,112,019. While microsurgical procedures are being performed, a number of personnel are moving around in the operating room. As such, exposing the cables an IV pole increases the risk of damage caused by personnel or other objects bumping into the system or by impacting the system into walls or other obstructions during transport.

SUMMARY OF THE INVENTION

Among the several objectives and features of the present invention may be noted the provision of a microsurgical system which includes a cart for supporting and transporting the operating components of the present system; the provision of such a system in which selected operating components can be quickly installed on or removed from the cart to configure the system for use in performing selected surgical procedures; the provision of such a system for which a configured system is easily transportable on the cart without disassembling the system; the provision of such a system in which peripheral and other items are carried within the cart; the provision of such a system in which the cart and components carried by the cart are protected against damage; and the provision of such a system which is more cost effective and space efficient for performing multiple types of microsurgical procedures.

DETAILED DESCRIPTION OF PREFERRED EMBODIMENTS

Figure 1:
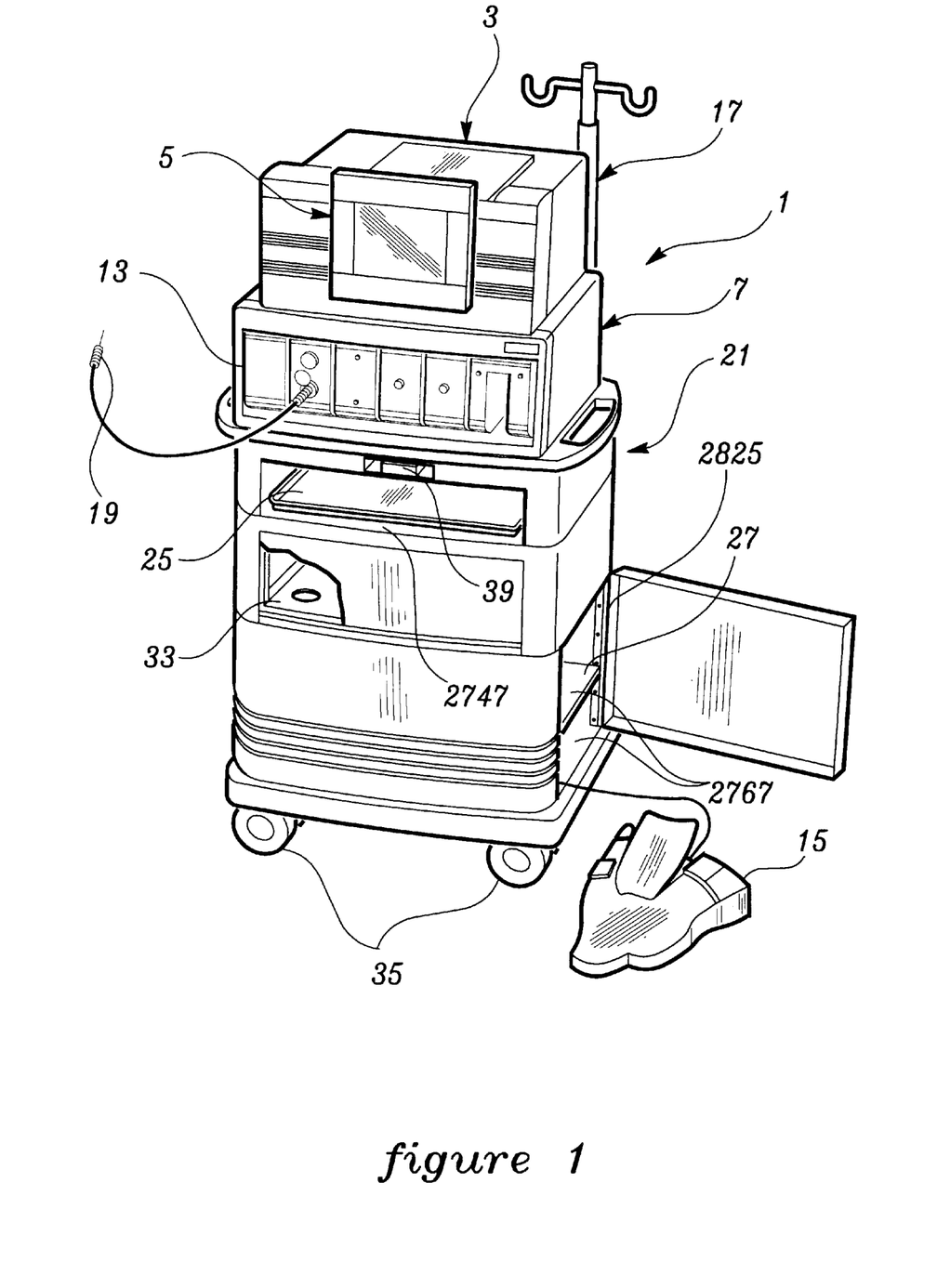
FIG. 1 is a perspective view of a microsurgical control system for use with ophthalmic microsurgical instruments.

As shown in FIG. 1, the cart 21 of this invention is used for supporting and transporting the components of the present system. The cart includes the aforementioned surgical, or Mayo, tray 25, the automated IV pole assembly 17, the storage compartment 27 for stowing the foot pedal control assembly 15, disposable packs (not shown) and other items, the expansion compartment 33 for housing the expansion base unit 207 (FIG. 2), and casters 35. Base unit 7 and computer unit 3 preferably sit on top of the cart 21 as shown in FIG. 1 and the Mayo tray 25 is mounted on an articulating arm (not shown) attached to the top of cart 21, directly beneath the base unit 7. The cart 21 also holds a remote control transmitter for remotely controlling the present system.

Referring to FIGS. 2–7, the cart 21 has a generally rectangular base, designated 2701, a front wall 2703, a rear wall 2705, opposite side walls 2707, 2709 and a top wall 2711 having an upper surface 2713 for supporting the base unit 7 and the computer unit 3 (each of the walls being generally designated by their respective references). The front wall 2703, rear wall 2705 and side walls 2707, 2709 of the cart 21 define an interior space which is divided into the lower storage compartment 27 (FIG. 1), for storing peripherals such as the foot pedal control assembly 15, disposable packs and other items, and the upper expansion compartment 33, for receiving expansion base unit 207 which is substantially identical to the base unit 7 supported by the top wall 2711 of the cart 21. The cart 21 is designed to have a relatively low profile to facilitate maneuverability and to minimize the floor space required by the system 1 during use and storage. For example, the cart 21 shown in FIG. 1 is approximately 60 cm (24 inches) wide by 53 cm (21 inches) deep by 86 cm (34 inches) high. It is understood, however, that the dimensions of the cart 21 may be larger or smaller depending on the amount of equipment to be carried by the cart, and on other factors, without departing from the scope of this invention.

Figure 5:
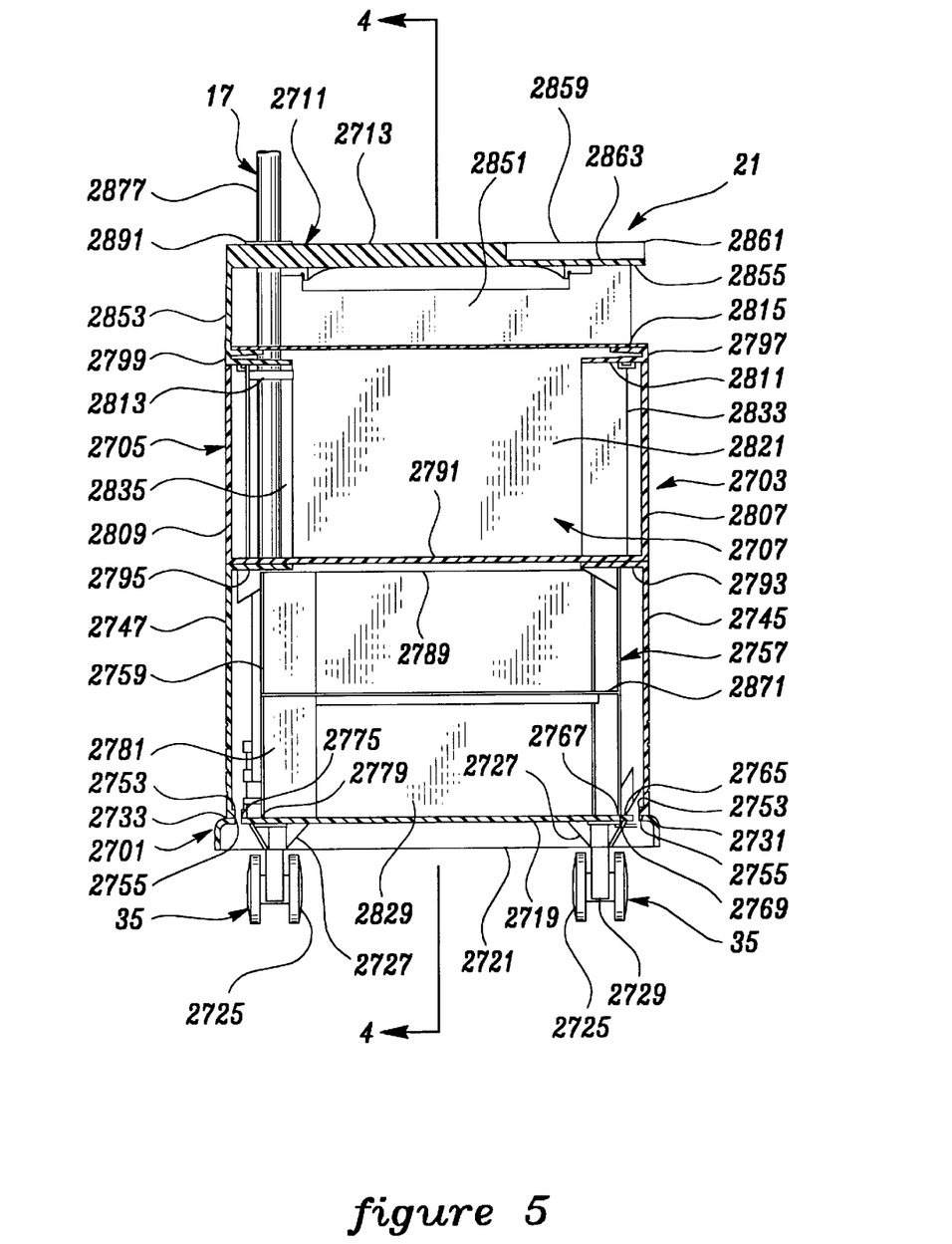
FIG. 5 is a cross-section taken in the plane of line 5—5 of FIG. 7.
Figure 6:
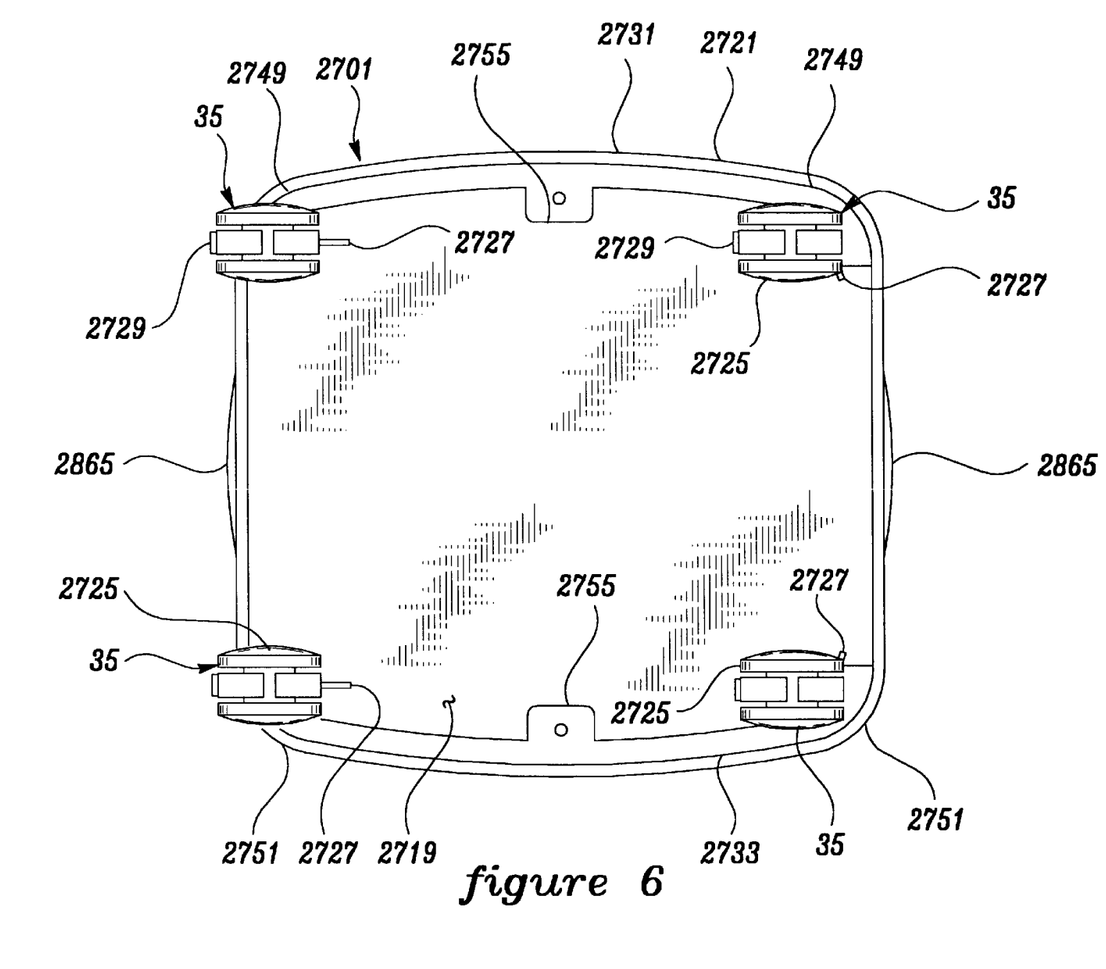
FIG. 6 is a bottom plan of the cart.

As best seen in FIG. 6, the base 2701 of the cart 21 comprises a generally rectangular floor plate 2719 having downwardly turned edges defining a peripheral skirt 2721 (FIG. 2) around the base which functions as a bumper for the cart. The front and rear edges of the base 2701 may have a slight outward curvature. The floor plate 2719 and skirt 2721 may be fabricated as an integral metal (e.g., aluminum) casting. The base 2701 is movably supported by four (this number may vary) conventional casters, indicated generally as 35, each of which comprises a wheel 2725 mounted on a caster frame 2727 (FIG. 4) attached to the underside of the floor plate 2719 by suitable fasteners. Two of the casters 35 preferably have a locking mechanism 2729, as shown in FIG. 6, movable between a locked position in which the caster wheel 2725 is prevented from rolling, and an unlocked position in which the caster wheel is able to roll freely to allow the operator to maneuver the cart 21. Other types of wheels may used in place of the casters 35. Front and rear positioning grooves or channels, designated 2731 and 2733 in FIG. 5, respectively, are formed in the upper surface of the floor plate 2719 and extend in side-to-side direction with respect to the cart 21 adjacent its front and rear edges (the front channel 2731 being fully shown in FIG. 3). These channels 2731, 2733 receive the lower edges of the front and rear walls 2703, 2705 of the cart 21 and ensure proper positioning during assembly.

The front and rear walls 2703, 2705 of the cart 21 are preferably constructed of molded plastic, each comprising a pair of vertical corner posts (the front corner posts being designated 2735a, 2735b in FIG. 2, and the rear corner posts being designated 2737a and 2737b in FIG. 7) extending up from the floor plate 2719 at opposite sides of the base 2701, and a lower panel 2743, 2745 extending between the lower portions of the two corner posts. The lower panels 2743, 2745 may be formed to have a slight outward curvature according to the curvature of the front and rear edges of the base 2701. The front and rear corner posts 2735a, 2735b, 2737a, 2737b have lower ends formed with feet 2747 (the foot of rear cornerpost 2737a being shown in FIG. 3) which are received in respective front and rear depressed corner areas 2749, 2751 of the floor plate 2719 and secured in place by fasteners extending through the feet and floor plate. As further seen in FIG. 3, the front depressed corner areas 2749 of the floor plate 2719 are connected by the front positioning channel 2731 in the floor plate. Similarly, the rear depressed corner areas 2751 are connected by the rear positioning channel 2733 in the floor plate 2719. Additional feet, designated 2753 in FIG. 5, are centrally formed along the bottom of each of the front and back walls 2703, 2705 to be received in centrally located depressions 2755 (FIG. 6) within the front and rear positioning channels 2731, 2733 of the floor plate 2719.

To provide additional structural strength to the cart, the lower panels 2743, 2745 of the front and rear walls 2703, 2705 are lined with reinforcing liners of suitably rigid sheet material (e.g., sheet metal), the liner for the lower front panel being designated 2757, and the liner for the lower rear panel being designated 2759. As shown best in FIG. 3, the front liner 2757 has a substantially flat central portion 2761 lying in a generally vertical plane, and a pair of L-shaped flanges 2763 extending vertically along opposite sides of the liner. These flanges 2763 are connected to the front corner posts 2735a, 2735b by fasteners. A rib 2765 is integrally formed with the floor plate 2719 adjacent the front positioning channel 2731 and extends between the front depressed corner areas 2749 of the floor plate. Upwardly extending tabs 2767 (one of which is shown in FIG. 5) are also integrally formed with the floor plate 2719 and cooperate with the rib 2765 to define a slot 2769 (FIG. 5) between the tabs and the rib for receiving the lower edge of the central portion 2761 of the front liner 2757 to properly position the liner on the base 2701.

Figure 3:
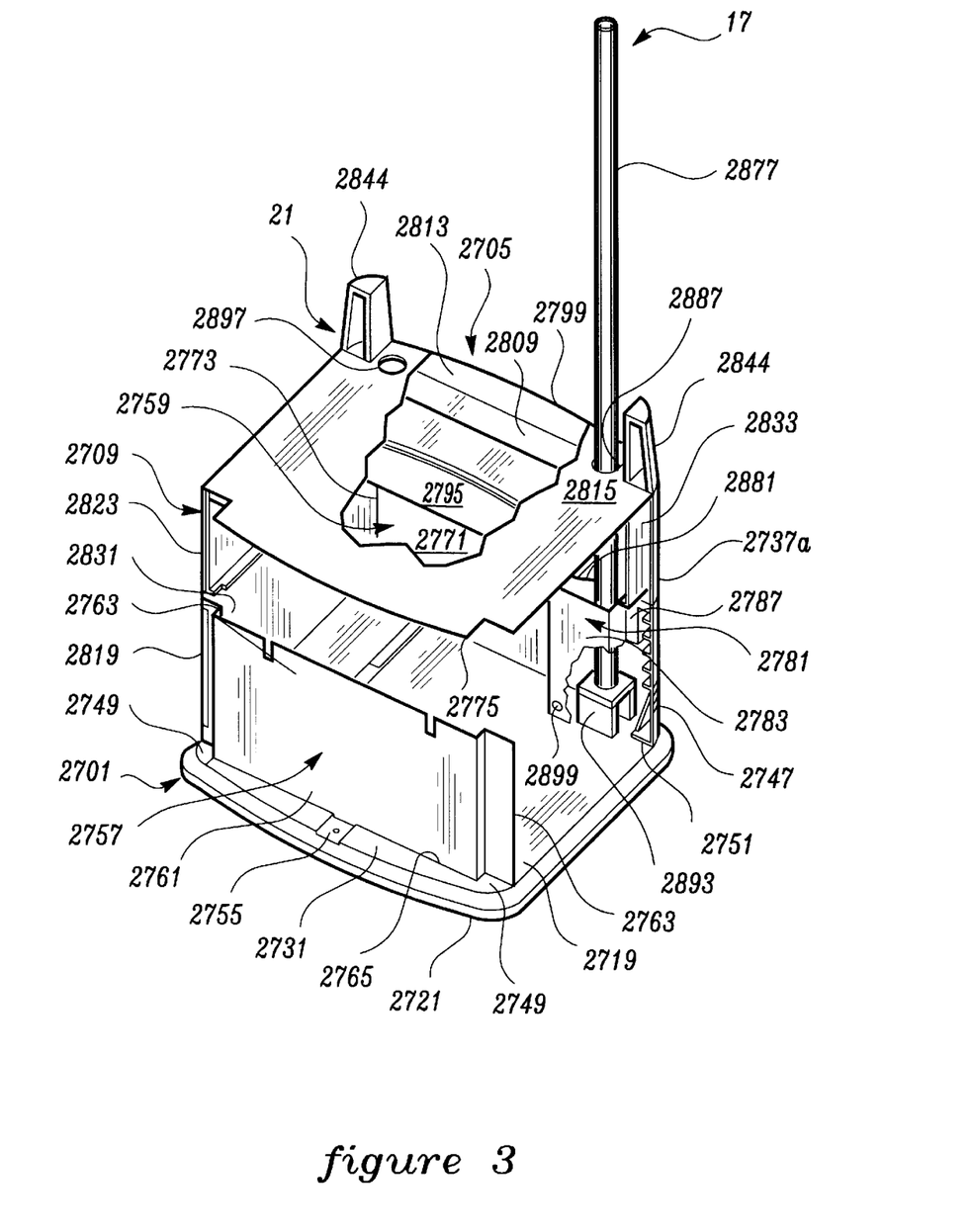
FIG. 3 is a perspective of the cart shown in FIG. 1 with various parts removed or fragmented to reveal internal construction of the cart.

Again referring to FIG. 3, the rear liner 2759 has a substantially flat central portion 2771 lying in a generally vertical plane, and an L-shaped flange 2773 extending vertically along a left (as viewed in FIG. 3) side of the liner. The L-shaped flange 2773 is connected to the left rear corner post 2737b by fasteners. A rib 2775 (FIG. 5) is integrally formed with the floor plate 2719 adjacent the rear positioning channel 2733 and extends side-to-side with respect to the floor plate between the rear depressed corner areas 2751. Upwardly extending tabs, designated 2777 in FIG. 3 are also formed integrally with the floor plate 2719 and cooperate with the rib 2775 to define a slot 2779, as shown in FIG. 5 between the tabs and the rib, for receiving the lower edge of the central portion 2771 of the rear liner 2759 to properly position the liner on the base 2701. An IV pole liner, designated 2781 in FIG. 3, has a generally U-shaped central portion 2783 and flanged end portions 2785, 2787, one of which is attached to the rear liner 2759 and the other of which is attached to the rear corner post 2737a of the rear wall 2705. The rear liner 2759 and IV pole liner 2781 together form a protective casing for shielding the IV pole assembly 17 against damage by other equipment carried loosely within the interior space of the cart 21. As best seen in FIG. 3, a horizontal beam 2789 extends between the front and rear liners 2757, 2759 and is fastened to the liners adjacent their upper edges to support the liners in position and maintain their spacing relative to one another.

Support structure comprising an expansion shelf 2791 (FIG. 2) is provided in the cart 21 for supporting the aforementioned expansion base unit 207. Referring to FIG. 5, this shelf 2791, which is also preferably a molded plastic part, is supported by a pair of flat shelf supports 2793, 2795 extending horizontally inwardly into the interior of the cart 21 from the front and rear walls 2703, 2705, generally adjacent the upper edges of the lower panels 2743, 2745. The beam 2789 extending between the front and rear liners 2757, 2559 is rabbeted at its ends to receive these shelf supports 2793, 2795 so that the upper surfaces of the supports are generally flush with the upper surface of the beam to provide a continuous co-planar surface for stably supporting the expansion shelf 2791, the latter of which defines the floor of the expansion compartment 33.

Referring to FIGS. 271 and 276, each of the front and rear walls 2703, 2705 of the cart 21 also includes a horizontal cross member 2797, 2799 which connects the two corner posts 2735a, 2735b and 2737a, 2737b of each wall, adjacent the upper ends of the posts. The cross members 2797, 2799 are spaced above the upper edges of the front and rear lower panels 2743, 2745 to define, in conjunction with the corner posts 2735a, 2735b, 2737a, 2737b, rectangular openings 2801, 2803 in the front and rear walls 2703, 2705 of the cart 21 through which expansion base unit 207 (FIG. 2) may be placed on the expansion shelf 2791. The shelf 2791 has depressions 2805 (FIG. 2) therein for receiving feet (not shown) on the bottom of the expansion base unit 33 to maintain the base unit in a fixed and stable position on the shelf. When an expansion base unit 33 is not needed, the openings 2801, 2803 in the front and back walls 2703, 2705 of the cart 21 are preferably closed by removable closure panels 2807, 2809 (FIG. 5) suitably securable to the cart. In the preferred embodiment of the invention, the lower panel 2743, 2745, corner posts 2735a, 2735b, 2737a, 2737b and cross member 2797, 2799 of each of the front and rear walls 2703, 2705 are fabricated as a single molded part of suitable plastic, but this is not essential to the present invention.

Figure 2:
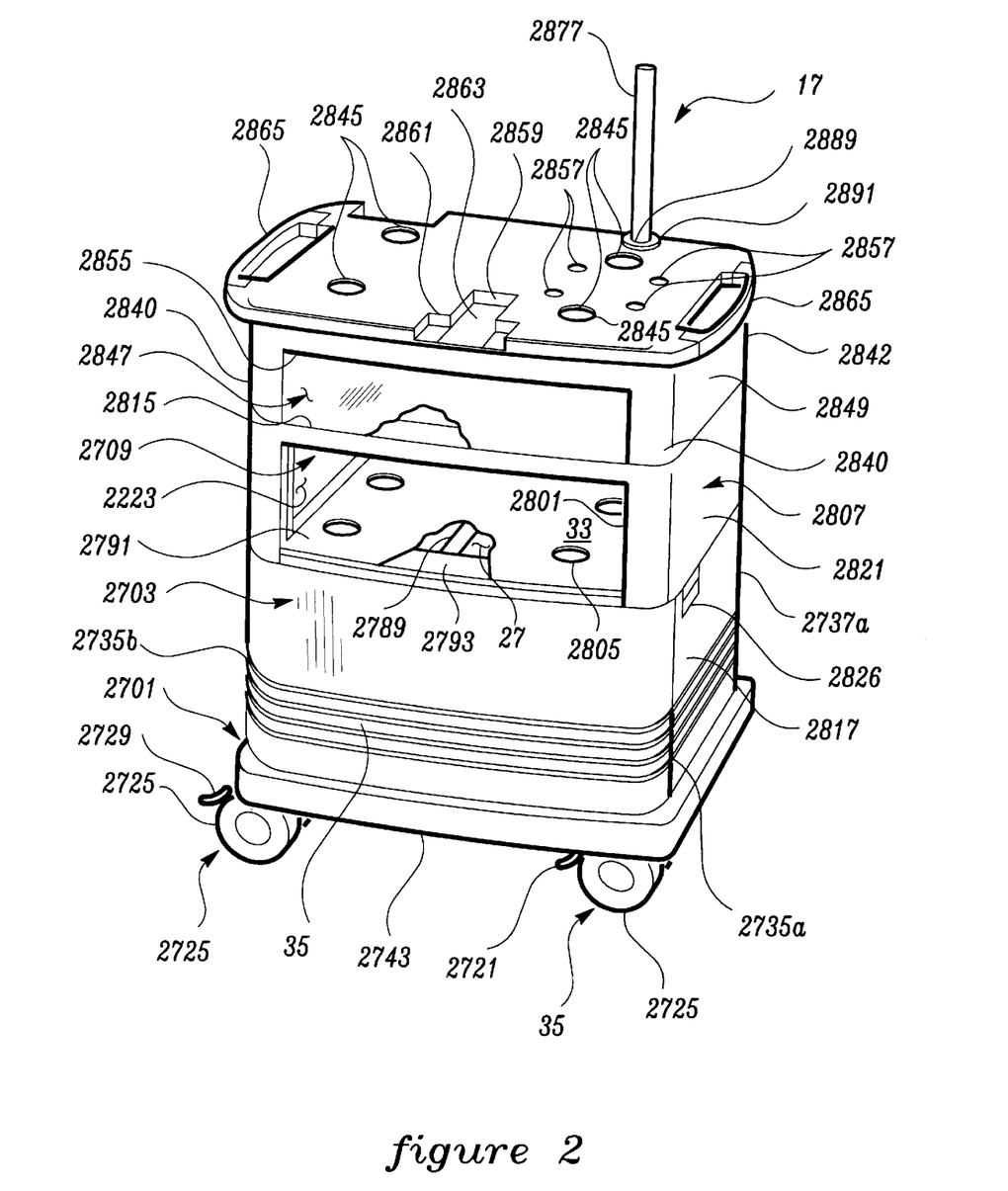
FIG. 2 is a perspective of a cart of this invention.

Referring still to FIG. 5, a pair of horizontal cover panel supports 2811, 2813 similar to the shelf supports 2793, 2795 extend inwardly into the interior space of the cart 21 from the front and rear cross members 2797, 2799. These supports 2811, 2813 support a cover panel 2815 in a position spaced a suitable distance above the expansion shelf 2791. As shown in FIG. 2, this cover panel 2815 forms the ceiling of the aforementioned expansion compartment 33. The cover panel supports 2811, 2813 are preferably molded as integral parts of respective cross members 2797, 2799. The cover panel 2815 may be permanently fixed in the cart 21 or it may be removable, in which case the top wall 2711 of the cart will form the ceiling of the expansion compartment 33.

Now referring to FIGS. 271 and 273, the side walls 2707, 2709 of the cart 21 comprise generally rectangular side doors 2817, 2819 and side panels 2821, 2823 preferably constructed of the same molded plastic as the front and rear walls 2703, 2705. The side door 2817 at the right side of the cart 21 (as viewed in FIG. 2) is mounted on the rear corner post 2737a by means of a hinge 2825 (FIG. 1) for swinging between a closed position in which the door closes the space between the right front and right rear corner posts 2735a, 2737a above the floor plate 2719, and an open position for providing access to the interior of the cart 21 from the right side of the cart. The side door 2819 at the left side of the cart 21 (as viewed in FIG. 4) is mounted on the front corner post 2735b (FIG. 2) by means of a similar hinge (not shown) for swinging between a closed position in which the door closes the space between the left front and left rear corner posts 2735b, 2737b above the floor plate 2719, and an open position for providing access to the interior of the cart from the left side of the cart. As seen best in FIG. 2, each of the side doors 2817, 2819 can be releasably secured in its closed position by a suitable door latch 2826, 2828. Like the front and back walls 2703, 2705 of the cart 21, the side doors 2817, 2819 are preferably lined with rigid door liners 2829, 2831 (e.g., sheet metal liners) to provide additional structural strength. These liners 2829, 2831 (FIG. 4) are attached to the inside of the door 2817, 2819 by suitable means (e.g., mechanical fasteners).

Figure 4:
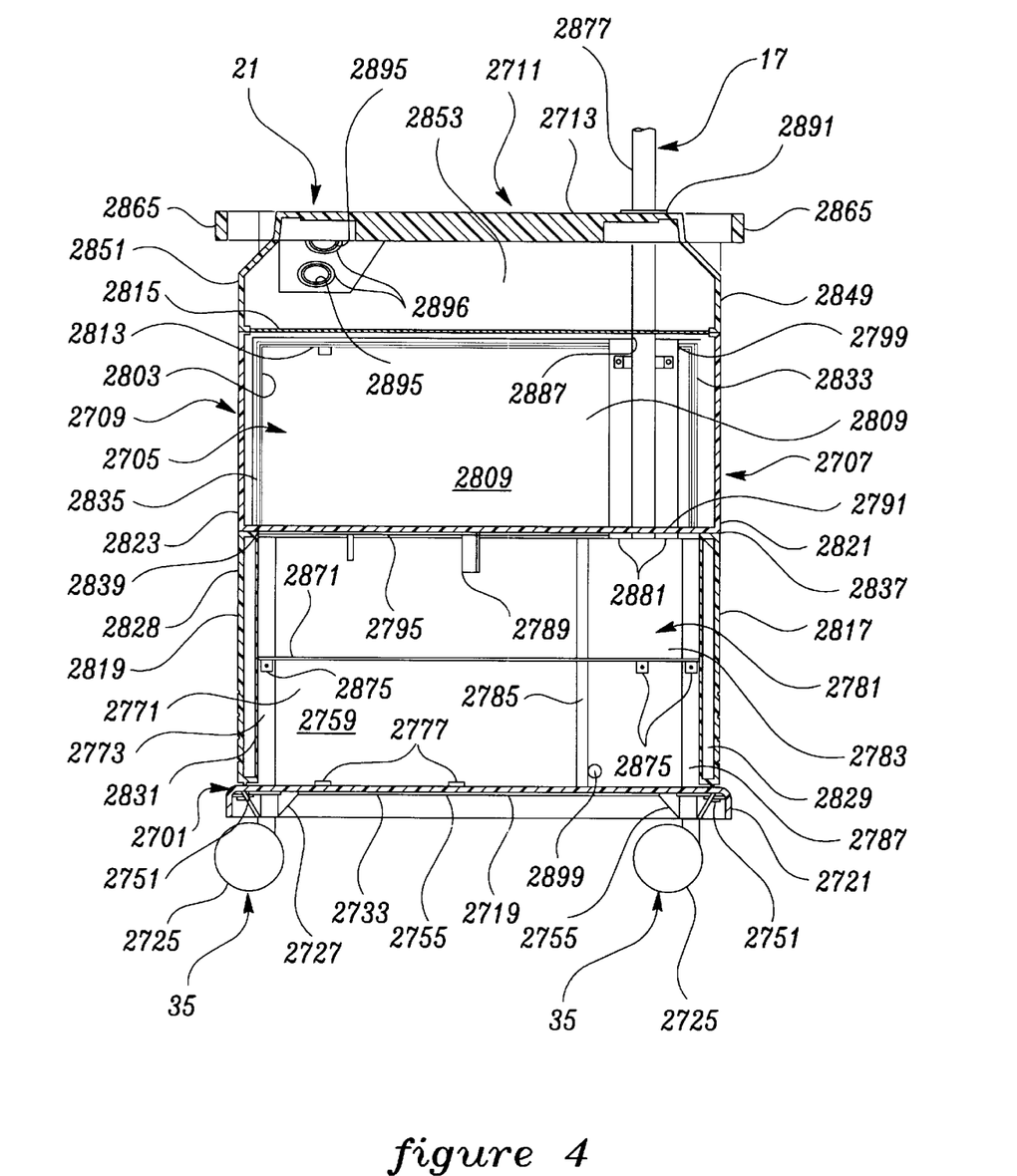
FIG. 4 is a cross-section taken in the plane of line 4—4 of FIG. 5.

Still referring to FIG. 4, the side panels 2821, 2823 of the side walls 2807, 2809 are disposed immediately above the side doors 2817, 2819 and define the sides of the expansion compartment 33. The side panels 2821, 2823 are secured in overlapping relation to vertical flaps 2833, 2835 on the front and rear walls 2703, 2705 by suitable fasteners. The flaps 2833, 2835 are preferably integrally formed with respective cornerposts 2735a, 2735b, 2737a, 2737b and extend vertically between the shelf supports 2793, 2795 and the cover panel supports 2811, 2813. The bottoms of the side panels 2821, 2823 are formed with depending vertical lips 2837, 2839 against which the upper edge margins of the side doors 2817, 2819 seat when they are closed, thus ensuring that the exterior surfaces of the side doors are flush with the exterior surfaces of the respective side panels thereabove.

The top wall 2711 of the cart 21, which supports the base unit 7 and computer unit 3, is generally rectangular and has depending legs (the front legs being designated in FIG. 2 as 2840 and the rear legs being designated in FIG. 7 as 2842) at its four corners. Each leg 2840, 2842 has a vertical hole (not shown) in it which opens downwardly to receive a connecting pin or peg, designated 2844 in FIG. 3, extending up from a respective corner post 2735a, 2735b, 2737a, 2737b, the holes being sufficiently deep that the bottoms of the legs seat securely on the tops of the corner posts. The legs 2840, 2842 have an exterior configuration at their lower ends similar to that of the corner posts 2735a, 2735b and 2737a, 2737b at their upper ends so that when the legs are fully seated on the corner posts, the legs and posts have a visual continuity. Like the expansion shelf 2791, the top wall 2711 preferably has depressions 2845 (FIG. 2) in it for receiving feet (not shown) on the bottom of the base unit 7.

As further illustrated in FIGS. 271 and 273, the top wall 2711 is spaced above the cover panel 2815 to define a compartment 2847 for the Mayo tray 25 (FIG. 1). This compartment 2847 is closed at the sides of the cart 21 by side panels 2849, 2851 extending between the front and rear legs 2840, 2842 of the top wall 2711, and at the rear of the cart by a rear panel 2853 extending between the rear legs 2842 of the top wall. In the preferred embodiment, the top wall 2711, top side panels 2849, 2851, top rear panel 2853 and corner legs 2840, 2842 are fabricated as a single molded part of suitable plastic, but this is not essential to the present invention. The Mayo tray compartment 2847 is accessible through an opening 2855 at the front of the cart 21. The articulating arm (not shown) holding the Mayo tray 25 is pivotally mounted on a support (not shown) attached to the underside of the top wall 2711 by fasteners extending through holes 2857 in the top wall, the arrangement being such that the arm can be pivoted between a stored position in the compartment and a position outside the compartment in which the tray is accessible. Construction and operation of the articulated Mayo tray 25 is well known to those skilled in the art and will not be further described herein.

Referring to FIG. 2, a generally T-shaped recess 2859 is formed in the upper surface 2713 of the top wall 2711 of the cart 21 adjacent the front of the cart for holding the remote control transmitter 39 (FIG. 1). The head 2861 of the recess 2859 along the front edge of the top wall 2711 is wider than the transmitter 39 to provide sufficient clearance to permit the transmitter to be readily grasped and removed from the recess. The recess 2859 has an inclined bottom surface 2863 which slopes downwardly and rearwardly away from the front edge of the top wall 2711 to inhibit the transmitter 39 from falling off the cart 21. A pair of handles 2865 are provided at opposite sides of the top wall 2711 of the cart 21 for facilitating maneuvering the cart.

As shown in FIGS. 1 and 273, the storage compartment 27 between the floor plate 2719 and the expansion shelf 2791 may be divided into multiple compartments 2867 by a storage shelf 2871 having notched corners (not shown) for accommodating the L-shaped flanges 2763, 2773 of the front and rear liners 2757, 2759 and the IV pole liner 2781. As further seen in FIG. 4, the storage shelf 2871 is fastened to the front liner 2757, rear liner 2759 and IV pole liner 2781 by fasteners extending through tabs 2875 projecting down from the notched corners of the shelf.

With reference to FIG. 3, the IV pole assembly 17 comprises a vertical IV pole 2877 which extends from the floor plate 2719 up through the interior of the cart 21 and through the top wall 2711 of the cart. The rear shelf support 2795, rear cover panel support 2813 and cover panel 2815 have notches (designated 2881, 2885, 2887, respectively) through which the IV pole 2877 extends. The expansion shelf 2791 also has a similar notch (not shown). The top wall 2711 has a large opening 2889 (FIG. 2) with a grommet insert 2891 through which the IV pole 2877 passes as it extends upward through the top wall of the cart 21. The IV pole assembly 17 is described in detail in U.S. Pat. No. 5,122,019, which is incorporated herein by reference. A stand 2893 for supporting the IV pole 2877 upright is positioned on the floor plate 2719 within the casing formed by the rear liner 2759 and IV pole liner 2781. The stand 2893 is attached by fasteners to the rear liner 2759. A variable speed motor (not shown) within the casing drivingly extends and retracts the IV pole 2877 depending on the fluid pressure required during a particular surgical procedure. Operation of the motor is controlled by an IV pole control module (not shown) within the casing.

Figure 7:
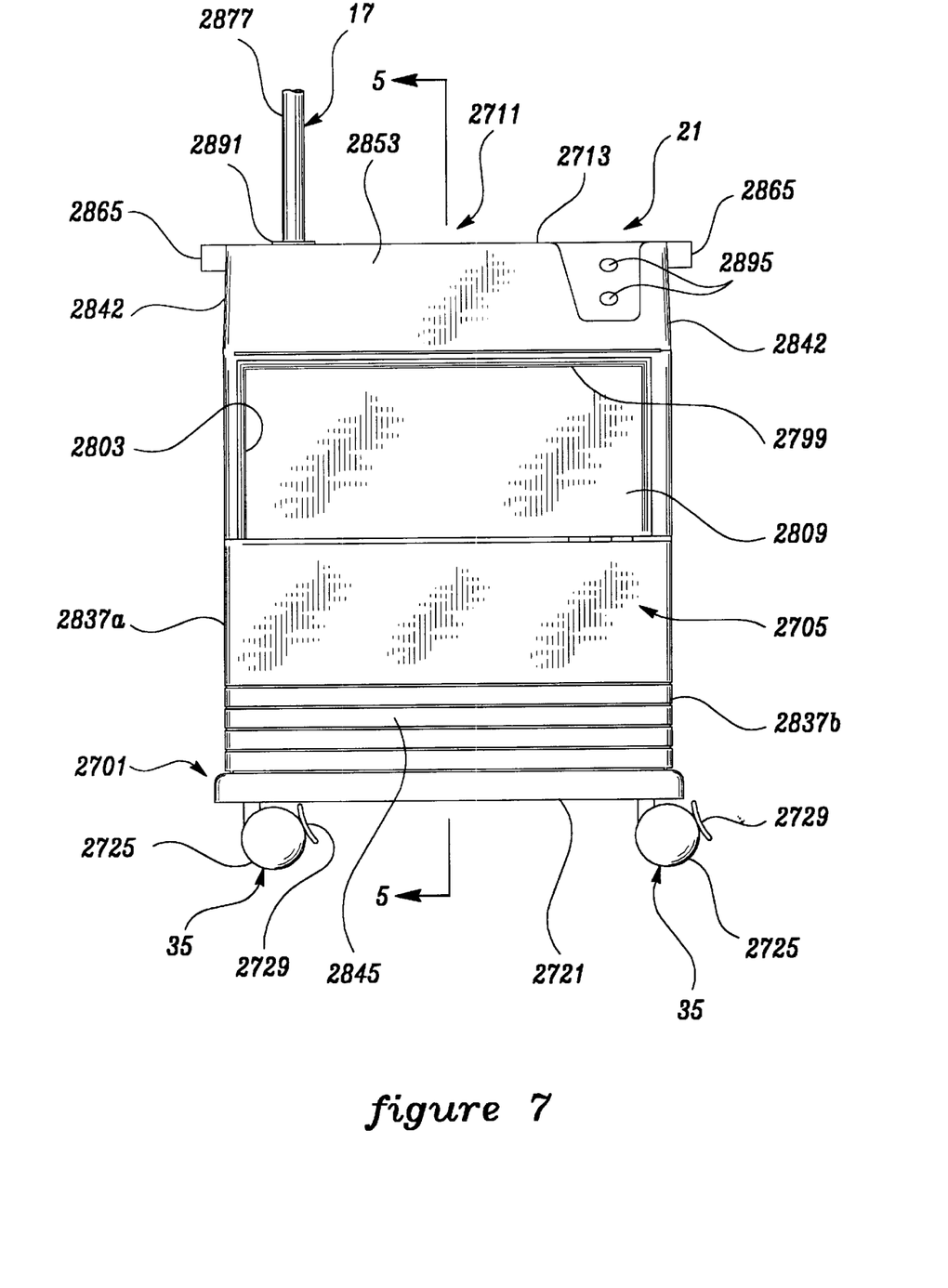
FIG. 7 is a rear elevation of the cart.

Electrical cables run throughout the interior space of the cart 21 to interconnect the various components of the system. As shown in FIG. 7, the top wall 2711 has a pair of openings 2895 with grommet inserts 2896 to allow passage of cables connected to the base unit 7 and computer unit 3. Cable access into the expansion compartment 33 is provided through an opening 2897 (FIG. 3) in the cover panel 2815 and through a notch 2898 in the rear cover panel support 2813. Cable access into the storage compartment 27 for connection to the IV pole assembly 17 and foot pedal control 15 is provided by the notch in the expansion shelf 2791 and the notch 2881 in the rear expansion support 2795 through which the IV pole 2877 passes. An opening 2899 in the IV pole liner 2781 allows cables from the foot pedal control 15 to connect with the IV pole control module within the casing formed by the rear liner 2859 and the IV pole liner.

To configure a microsurgical system of the present invention as shown in FIG. 1, a base unit 7 is placed onto the top wall 2711 of the cart 21 by seating the feet on the bottom of the base unit into the depressions 2845 in the upper surface 2713 of the top wall of the cart. The computer unit 3 is seated on top of the base unit 7. The desired control modules 13 for controlling the surgical instruments 19 are inserted into the base unit 7. When additional space for control modules 13 is required, the front and rear closure panels 2807, 2809 of the cart 21 are removed and the expansion base unit (not shown) is inserted into the expansion compartment 33 within the cart. The feet of the base unit 7 are received by the depressions 2805 in the expansion shelf 2791 to secure the expansion base unit within the cart 21. When the foot pedal control assembly 15 is used, the side doors 2817, 2819 of the cart are opened and the foot pedal control is removed from the storage compartment 27. The electrical cables are connected to the various operating components and the rear closure panel 2809 is then secured in its closed position on the rear wall 2705 of the cart 21 (although this is not required for operation of the system). The front closure panel 2807 remains removed to provide access to the expansion base unit 207 for removably inserting control modules 13.

It is understood that one or more of the operating components may be removed from the cart 21, depending on the needs of the operator, without departing from the scope of this invention. For example, the system may include the cart 21, the computer unit 3 on the top wall 2711 and a base unit 7 carried within the expansion compartment 33. Additionally, one or more of the operating components may be located remote from the cart 21 and connected by electrical cables to operating components carried on or within the cart.

It will be observed from the foregoing that the cart 21 provides added flexibility to the microsurgical system 1 of the present invention and represents an improvement over conventional designs. Unlike the prior art systems in which a fully integrated console was placed on cart for transport, the present system has multiple, individual components which are removably installed on or within the cart 21 to provide the operator with increased flexibility in selecting and assembling a system geared toward particular surgical procedures. For example, one or more operating components may be selected by the operator, according to the particular procedure being performed, and quickly installed on or within the cart 21. The cart 21 can be easily moved to and from remote locations where the surgical procedures are performed, without removing the equipment from the cart. Additionally, the removability of the operating components from the cart 21 allows the operator to quickly reconfigure the system supported by the cart for use in performing other surgical procedures.

Providing an expansion compartment 33 for the installation of expansion base unit allows for quick expansion of the system 1 to include additional instruments 19 for performing the surgical procedures. Also, the openings 2895, 2897 in the top wall 2711 and cover panel 2815, as well as the notches 2885, 2883, 2881 in the rear cover panel support 2813, expansion shelf 2791 and rear expansion shelf support 2795, allow the cables of the system 1 to run throughout the interior of the cart 21, to reduce the risk of damage to the cables caused by bumping into walls or being impacted by other equipment. Integrating the IV pole assembly 17 into the interior of the cart 21 similarly reduces the risk of damage to the assembly. The storage compartment 27 within the cart allows the foot pedal control 15, disposable packs and other items to be carried with the cart for convenience and for reducing the risk that these items will become lost or separated from the system. The structure of the cart 21 also inhibits damage caused by bumping the cart into walls or other obstructions during transport.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A microsurgical system comprising:
   a cart having a base, wheels on the base, a front wall, rear wall and side walls defining an interior space above the base, and a top wall for supporting electronic equipment for use with one or more electronically controlled surgical instruments;
   an opening in the front wall of the cart;
   support structure in said interior space positioned immediately rearward of the opening in the front wall; and
   a base unit in said interior space supported by said support structure, said base unit comprising a base unit housing and one or more electronic control modules removably insertable in the base unit housing for controlling said surgical instruments.

2. A microsurgical system as set forth in claim 1 further comprising a removable front closure panel for closing the opening in the front wall of the cart.

3. A microsurgical system as set forth in claim 2 further comprising an opening in the rear wall of the cart providing access to the support structure, and a removable rear closure panel for closing the opening in the rear wall.

4. A microsurgical system as set forth in claim 1 wherein said cart has at least one cable opening therein to permit passage of electrical cable between said base unit and said electronic equipment on the top wall of the cart.

5. A microsurgical system as set forth in claim 1 wherein the cart has an IV pole mounted within said interior space and extending up through an opening in the top wall of the cart, and a mechanism for effecting vertical extension and retraction of the IV pole.

6. A microsurgical system as set forth in claim 1 wherein said support structure comprises a horizontal shelf extending between the front and rear walls of the cart.

7. A microsurgical system as set forth in claim 6 wherein said shelf is configured for removably holding said base unit housing in a fixed and stable position on the shelf.

8. A microsurgical system as set forth in claim 6 wherein said support structure further comprises a first horizontal shelf support integrally formed with the front wall of the cart and extending into said interior space and a second horizontal shelf support integrally formed with the rear wall and extending into said interior space, said shelf supports cooperating to support the shelf in a generally horizontal position.

9. A microsurgical system as set forth in claim 6 wherein the horizontal shelf divides the interior space within the cart into an expansion compartment above the shelf for receiving said base unit, and a storage compartment below the shelf.

10. A microsurgical system as set forth in claim 9 further comprising a storage shelf extending between the front and rear walls of the cart within the storage compartment to divide said storage compartment into a plurality of individual compartments.

11. A microsurgical system as set forth in claim 9 wherein one of the side walls of the cart comprises a door movable between a closed position and an open position for accessing said storage compartment.

12. A microsurgical system as set forth in claim 1 further comprising handles on the cart at opposite sides of the top wall of the cart for facilitating movement of the cart.

13. A microsurgical system as set forth in claim 1 further comprising a second opening in the front wall of the cart immediately below said top wall, and a surgical tray in said interior space accessible through said second opening for holding surgical materials.

14. A microsurgical system as set forth in claim 1 wherein the top wall of the cart has depressions therein for removably holding said electronic equipment in a fixed and stable position on the top wall.

15. A microsurgical system as set forth in claim 1 further comprising a recess in the top wall of the cart for holding a remote control for said electronic equipment.

16. A microsurgical system as set forth in claim 1 wherein said base is of metal and said front, rear, side and top walls are of molded plastic.

17. A microsurgical system comprising:

a cart having a base, wheels on the base, a front wall, rear wall and side walls defining an interior space above the base, and a top wall;

electronic equipment on the top wall of the cart for use with one or more electronically controlled surgical instruments, said electronic equipment comprising a base unit having a base unit housing and one or more electronic control modules removably insertable in the base unit housing for controlling said surgical instruments;

an opening in the front wall of the cart;

support structure in said interior space of the cart positioned immediately rearward of the opening in the front wall;

an expansion base unit removably positioned in said interior space on the support structure, said expansion base unit comprising an expansion base unit housing and one or more expansion electronic control modules insertable into the expansion base unit housing for controlling said surgical instruments;

electrical cable connecting said expansion base unit and said electronic equipment; and at least one cable opening in the cart permitting passage of said electrical cable between said expansion base unit and said electronic equipment.

18. A microsurgical system as set forth in claim 17 wherein said top wall of the cart and said support structure are each configured to removably hold respective base units in fixed and stable positions.

19. A microsurgical system as set forth in claim 17 further comprising a removable front closure panel for closing the opening in the front wall of the cart.

20. A microsurgical system as set forth in claim 19 further comprising an opening in the rear wall of the cart providing access to the support structure, and a removable rear closure panel for closing the opening in the rear wall.

* * * * *